United States Patent [19]

Davis, Jr. et al.

[11] Patent Number: 5,058,425
[45] Date of Patent: Oct. 22, 1991

[54] EARTHEN CORE ANALYZING MEANS AND METHOD FOR DETERMINING THE METHANE STORAGE CAPACITY OF THE CORE

[75] Inventors: Lorne A. Davis, Jr., Houston; Gregory P. Pepin, Sugar Land; Robert M. Moss, Houston, all of Tex.

[73] Assignee: Texaco Inc., White Plains, N.Y.

[21] Appl. No.: 637,025

[22] Filed: Jan. 3, 1991

[51] Int. Cl.⁵ .............................................. E21B 49/02
[52] U.S. Cl. ........................................ 73/153; 73/38; 250/254; 250/255
[58] Field of Search ..................... 73/153, 38; 250/254, 250/255

[56] References Cited

U.S. PATENT DOCUMENTS

| | | | |
|---|---|---|---|
| 4,567,373 | 1/1986 | O'Meara, Jr. et al. | 250/573 |
| 4,671,102 | 6/1987 | Vinegar et al. | 73/61.1 R |
| 4,982,086 | 1/1991 | Withjack | 250/255 |
| 4,982,604 | 1/1991 | Davis et al. | 73/153 |

*Primary Examiner*—Robert Raevis
*Assistant Examiner*—W. Francos
*Attorney, Agent, or Firm*—Robert A. Kulason; James J. O'Loughlin; Ronald G. Gillespie

[57] ABSTRACT

An analyzer includes a test cell which contains a core of coal from a coal bed methane reservoir. A tomographic system is used for testing the core at different times and provides signals corresponding to the tests. While the earthen core is being tested, a fluid having the same size molecules as methane is provided to the earthen core as part of the testing. The signals from the tomographic system are used to determine the methane storage capacity of the core.

16 Claims, 1 Drawing Sheet

EARTHEN CORE ANALYZING MEANS AND METHOD FOR DETERMINING THE METHANE STORAGE CAPACITY OF THE CORE

BACKGROUND OF THE INVENTION

Field of the Invention

The present invention relates to analyzing means and methods in general and, more particularly, analyzing means and methods for analyzing a core of material.

SUMMARY OF THE INVENTION

An analyzer includes a test cell which contains a core of methane adsorption material from a methane reservoir. A tomographic system is used for testing the core at different times and provides signals corresponding to the tests. While the core is being tested, a fluid having substantially the same size molecules as methane is provided to the earthen core as part of the testing. The signals from the tomographic system are used to determine the methane storage capacity of the core.

The objects and advantages of the invention will appear more fully hereinafter from a consideration of the detailed description which follows, taken together with the accompanying drawings wherein one embodiment of the invention is illustrated by way of example. It is t be expressly understood, however, that the drawings are for illustration purposes only and are not to be construed as defining the limits of the invention.

DESCRIPTION OF THE INVENTION

Figure 1:
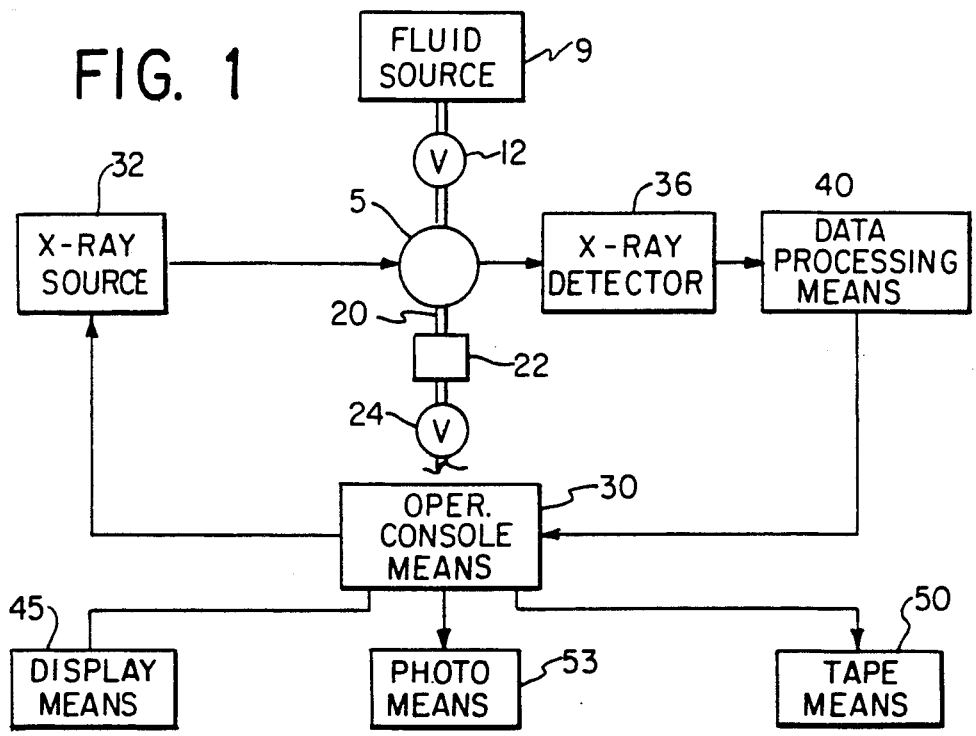
FIG. 1 is a simplified block diagram of a coal core analyzing system as constructed in accordance with the present invention.

With reference to FIG. 1, a test cell 5 containing a reservoir core 7 has connected to it a fluid source 9 by way of a line 12. Core 7 to be analyzed has been removed from a coal bed methane reservoir, or other methane adsorptive material such as shale, kerogen rich material or clay bearing material. The fluid should be the same size molecule as methane. Test cell 5 is initially evacuated through line 20. One such fluid is xenon gas. Other fluids may include krypton gas. The fluid over a finite period of time will fill test cell 5 to an established pressure by means of line 12, with line 20 now closed. Test cell 5 is filled to a desired fluid pressure, with the measurements observed from a pressure transducer 22, due to a closed valve 24 stopping the fluid from exiting. To drain the fluid from test cell 5, valve 24 is opened.

While the front of the fluid is passing through test cell 5 an operator's console means 30 is used to control an X-ray source 32 to irradiate the reservoir core 7 in test cell 5 with X-rays. X-rays passing through the reservoir core 7 in test cell 5 are detected by an X-ray detector 36 which provides a signal corresponding to the detected X-rays. The signal corresponding to the detected X-rays are provided to data processing means 40 which in turn provides data relating to the methane storage capacity of the reservoir core 7 to operator's console means 30. Operator console means 30 provides output signals to display means 45, to tape means 50 and photo means 53.

Figure 2:
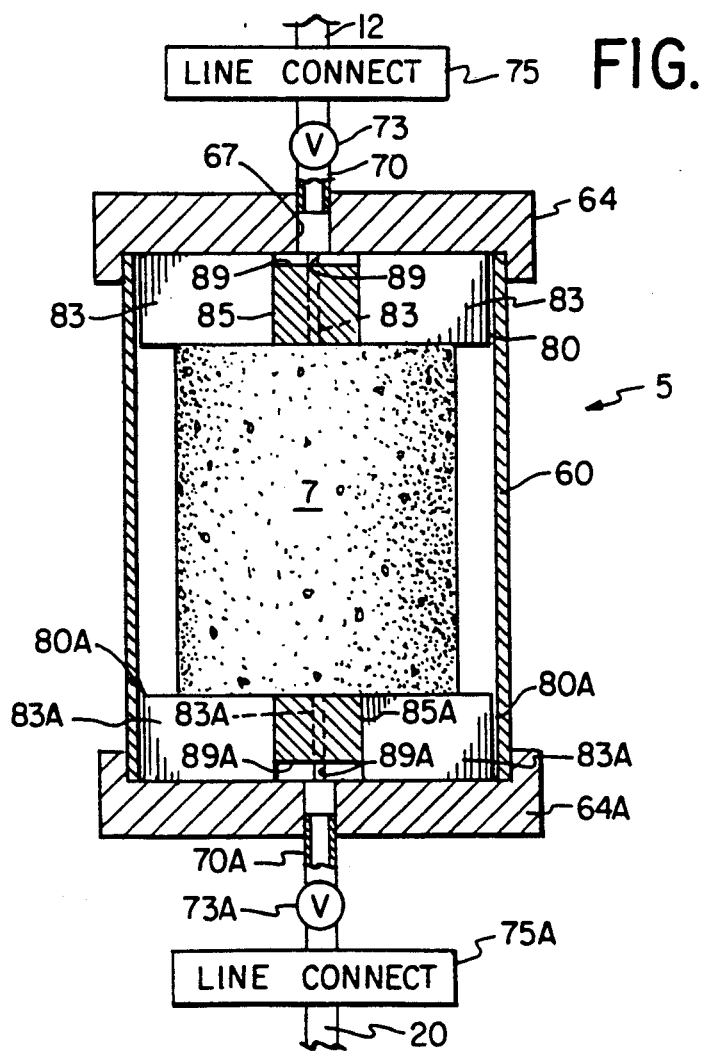
FIG. 2 is a detailed drawing of the test cell shown in FIG. 1.

With reference to FIG. 2 there is shown test cell 5 with the reservoir core 7 within it. Test cell 5 is filled to a desired fluid pressure, with the measurements observed from pressure transducer 22. Test cell 5 includes an end cap 64. End cap 64 includes a passageway 67 having a line 70 attached thereto. This permits flow of fluid through line 70 through passageway 67 and hence through end cap 64. In line 70 is a valve 73 and line 70 also has a line connector 75 which permits connection of line 70 to line 12.

Test cell 5 also includes another end cap 64a, another line 70a with a valve 73a and a line connector 75a. All elements having the same numeric identification but with a letter suffix operate in the same manner as elements bearing the same numeric designation without a letter suffix.

Also shown in FIG. 2 are spacers 80 and 80a. In the embodiment as shown, spacers 80 and 80a have four wings each, 83 and 83a respectively, with the center elements 85 and 85a, respectively. Center elements 85 and 85a have slots 89 and 89a, respectively, cut into them so that these slotted ends of spacers 80 and 80a may be placed against the passageways 67 and 67a, respectively. This allows fluid to flow from passageways 67 and 67a into the chamber formed by housing 60 and end caps 64, 64a. Any set of spacers that hold the core immobile, centered in the test cell while allowing the fluids to flow into the test cell around the sample, may be used. Thus, fluids flowing into test cell 5 will not only flow against the end of reservoir core 7 but will also pass around it so that it may also enter reservoir core 7 from either the end of core 7 or from the sides of reservoir core 7, depending on the permeability characteristic of reservoir core 7.

Let H correspond to the signal from X-ray detector.

$$(Hcg-Hco)/(Hg-Ho)=\phi+(1-\phi)(\rho a/\rho g)$$

where $\phi$ = core porosity (measured by liquid or assumed to be small (negligible)), Hcg is the CT number in Hounsfield units of reservoir core 7 filled with gas, Hco is the CT number of an evacuated reservoir core 7, Hg is the CT number of the gas at the established pressure, Ho is CT number of vacuum, $\rho g$ is the mass density of the gas at the established pressure, $\rho a$ is the desired end result, namely the mass density of the gas adsorbed on the coal (and/or held in a hydrate in the coal interstices) at the established pressure.

The storage capacity of the coal at the established pressure in grams of gas per cm$^3$ is $\rho a$.

$$\rho a = \frac{1}{(1-\phi)} \frac{(Hcg-Hco)}{(Hg-Ho)} - \frac{\phi}{(1-\phi)} + \rho g$$

What is claimed is:

1. A system for analyzing a core from an earthen methane reservoir, comprising:
   test cell means for containing the core of earthen material,
   tomographic means for testing the core at different times and providing signals corresponding thereto,
   means for providing a fluid to the core as part of the testing of the core, and
   storage capacity means for utilizing the signals from the tomographic means to determine a storage capacity of the core for methane.

2. A system as described in claim 1 further comprising: means for evacuating the core sample prior to testing, and means for controlling the pressure of the fluid in the core.

3. A system as described in claim 2 in which the storage capacity of the core is determined in accordance with the following equation:

$$pa = \frac{1}{(1-\phi)} \frac{(Hcg - Hco)}{(Hg - Ho)} - \frac{\phi}{(1-\phi)} + pg$$

where $p$ of a equals the storage capacity of the core in grams of gas per centimeter cubed, Hcg is the CT number in Hounsfield units of the reservoir core filled with gas, HCO is the CT number of an evacuated reservoir core, Hg is the CT number of the gas at the established pressure and Ho is the CT number of vacuum, $\phi$ is core porosity.

4. A system as described in claim 3 in which the material is methane adsorptive material.

5. A system as described in claim 4 in which the earthen core is coal.

6. A system as described in 4 in which the earthen material is shale.

7. A system as described in claim 4 in which the earthen material is kerogen rich.

8. A system as described in claim 4 in which the material is clay bearing material.

9. A method for analyzing a core from an earthen methane reservoir, comprising:
    containing the core of earthen material in test cell means,
    testing the core at different times with tomographic means,
    providing signals corresponding the testing of the core,
    providing a fluid to the core as part of the testing of the core, and
    utilizing the signals from the tomographic means to determine a storage capacity of the core for methane.

10. A method as described in claim 9 further comprising: evacuating the core sample prior to testing, and controlling the pressure of the fluid in the core.

11. A system as described in claim 10 in which the utilizing step includes: determining the storage capacity of the core in accordance with the following equation:

$$pa = \frac{1}{(1-\phi)} \frac{(Hcg - Hco)}{(Hg - Ho)} - \frac{\phi}{(1-\phi)} + pg$$

where $p$ of a equals the storage capacity of the core in grams of gas per centimeter cubed, 4 cg is the CT number in Hounsfield units of the reservoir core filled with gas, HCO is the CT number of an evacuated reservoir core, Hg is the CT number of the gas at the established pressure and Ho is the CT number of vacuum, $\phi$ is core porosity.

12. A method as described in claim 11 in which the containing step includes containing a core of adsorptive material.

13. A method as described in claim 11 in which the containing step includes containing a core of coal.

14. A method as described in 11 in which the containing step includes containing a core of shale.

15. A method as described in claim 11 in which the containing step includes containing a core cf kerogen rich material.

16. A method as described in claim 11 in which the containing step includes containing a core of clay bearing material.

* * * * *